United States Patent
Bailey et al.

(10) Patent No.: US 11,872,072 B2
(45) Date of Patent: Jan. 16, 2024

(54) TIMER CIRCUIT FOR X-RAY IMAGING SYSTEM

(71) Applicant: Siemens Medical Solutions USA, Inc., Malvern, PA (US)

(72) Inventors: Eric M. Bailey, North Hampton, NH (US); Jeffrey Johnson, West Newbury, MA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 310 days.

(21) Appl. No.: 17/282,159

(22) PCT Filed: Oct. 24, 2019

(86) PCT No.: PCT/US2019/057756
§ 371 (c)(1),
(2) Date: Apr. 1, 2021

(87) PCT Pub. No.: WO2020/106404
PCT Pub. Date: May 28, 2020

(65) Prior Publication Data
US 2022/0000444 A1     Jan. 6, 2022

Related U.S. Application Data

(60) Provisional application No. 62/769,116, filed on Nov. 19, 2018.

(51) Int. Cl.
*A61B 6/00* (2006.01)
*H05G 1/28* (2006.01)
*H05G 1/42* (2006.01)

(52) U.S. Cl.
CPC ............. *A61B 6/542* (2013.01); *A61B 6/56* (2013.01); *H05G 1/28* (2013.01); *H05G 1/42* (2013.01)

(58) Field of Classification Search
CPC   H05G 1/265; H05G 1/38; H05G 1/40; H05G 1/42; H05G 1/44; H05G 1/46;
(Continued)

(56) References Cited

U.S. PATENT DOCUMENTS 4,131,797 A     12/1978   Franke
5,808,376 A *   9/1998   Gordon .................... H02J 1/02
                                              307/64
(Continued)

FOREIGN PATENT DOCUMENTS

CN   104582574 A    4/2015
DE       550520 C   5/1932
(Continued)

*Primary Examiner* — Dani Fox
*Assistant Examiner* — Soorena Kefayati

(57) ABSTRACT

A timer circuit for an X-ray imaging system having an X-ray generator used to generate images of a patient. The circuit includes a current sensor connected between a main power system and a circuit interrupter, wherein the circuit interrupter is also connected to the X-ray generator. The circuit also includes a timing device coupled between the current sensor and a control computer. The timing device is triggered when a current level detected by the current sensor exceeds an idle current level wherein X-rays are not generated by the X-ray generator. The timing device then measures a time period that the idle current level is exceeded. When the measured time period exceeds a predetermined time period by 10%, the circuit interrupter is activated to turn off current flow to the X-ray generator.

19 Claims, 1 Drawing Sheet

(58) Field of Classification Search
CPC .. H05G 1/32; H05G 1/30; H05G 1/34; H05G 1/56; H05G 1/28; A61B 6/542; A61B 6/56; A61B 2560/0214; A61B 2560/0209; A61B 6/032; A61B 6/10
See application file for complete search history.

(56) References Cited

U.S. PATENT DOCUMENTS

| | | | | |
|---|---|---|---|---|
| 6,195,272 | B1* | 2/2001 | Pascente | H05G 1/22 363/131 |
| 2004/0247080 | A1* | 12/2004 | Feda | H05G 1/44 378/101 |
| 2007/0120498 | A1* | 5/2007 | Caiafa | H05G 1/52 315/248 |
| 2008/0159481 | A1* | 7/2008 | Yoshida | A61B 6/00 378/95 |
| 2012/0163546 | A1* | 6/2012 | Striker | H05G 1/46 378/110 |
| 2013/0315378 | A1* | 11/2013 | Yabugami | H05G 1/32 378/98 |
| 2014/0070812 | A1* | 3/2014 | Yokoi | A61B 6/56 324/322 |
| 2014/0254751 | A1* | 9/2014 | Yabugami | A61B 6/542 378/106 |
| 2014/0285927 | A1* | 9/2014 | Leung | H02H 3/16 361/42 |
| 2016/0240343 | A1* | 8/2016 | Mazellier | H01J 35/065 |
| 2016/0370225 | A1* | 12/2016 | Iwashita | H04N 5/32 |
| 2017/0223814 | A1* | 8/2017 | Matilaine | H05G 1/34 |
| 2018/0042097 | A1* | 2/2018 | Kim | A61B 6/56 |
| 2018/0092617 | A1* | 4/2018 | Schwartz | A61B 6/4085 |
| 2018/0199421 | A1* | 7/2018 | Kim | H02H 7/18 |
| 2018/0315579 | A1* | 11/2018 | Yonezawa | H05G 1/54 |
| 2018/0332696 | A1* | 11/2018 | Kim | A61B 6/56 |
| 2019/0044336 | A1* | 2/2019 | Wagner | A61B 6/56 |
| 2021/0227675 | A1* | 7/2021 | Murakami | H05G 1/46 |

FOREIGN PATENT DOCUMENTS

| | | |
|---|---|---|
| DE | 10209043 A1 | 9/2003 |
| DE | 102016110948 A1 | 12/2016 |
| JP | H06223995 A | 8/1994 |
| JP | H05317297 A | 12/1999 |
| JP | 2003302716 A | 10/2003 |
| JP | 2017202034 A | 11/2017 |
| WO | 2009116949 A1 | 9/2009 |

* cited by examiner

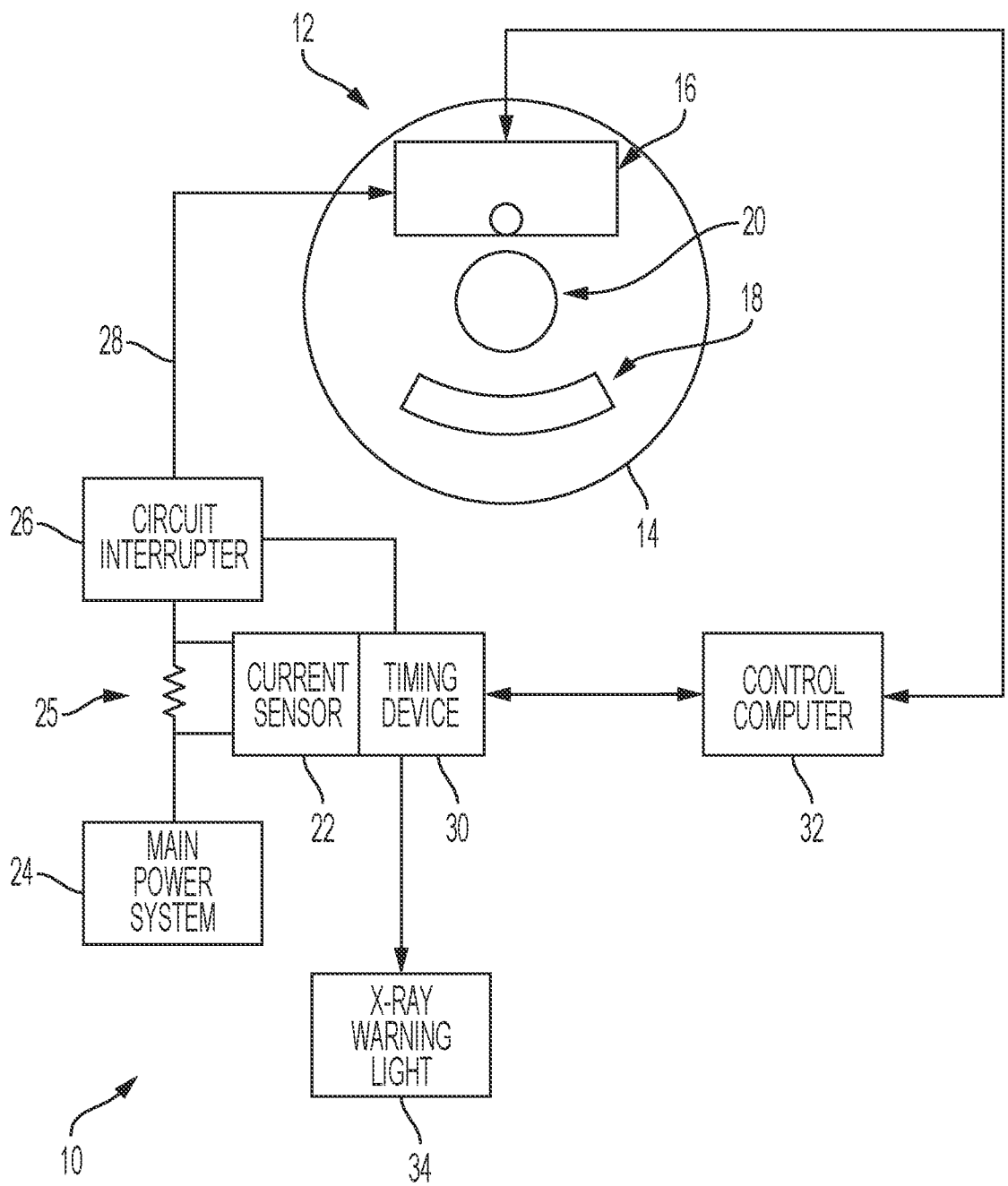

TIMER CIRCUIT FOR X-RAY IMAGING SYSTEM

PRIORITY CLAIM

This application is a U.S. National Phase Application of PCT/US2019/057756 filed on Oct. 24, 2019, which claims the benefit of U.S. Provisional Application No. 62/769,116 filed on Nov. 19, 2018, which is incorporated herein by reference in its entirety and to which this application claims the benefit of priority.

TECHNICAL FIELD

Aspects of the present invention relate to a timer circuit for an X-ray imaging system, and more particularly, to a timer circuit having a current sensor and a timing device that is triggered when a current level detected by the current sensor exceeds a predetermined current level of the X-ray imaging system wherein the timing device measures a time period that the predetermined current level is exceeded and when the measured time period exceeds a predetermined time period the circuit interrupter is activated to turn off current flow to the X-ray generator.

BACKGROUND

X-ray medical imaging systems such as computed tomography (CT) systems are required by government regulatory agencies such as the Food and Drug Administration (FDA) and the International Electrotechnical Commission (IEC) to have two different methods to monitor and control the generation of X-rays. The methods provide primary and backup methods to stop the generation of, or terminate, X-rays so that a patient is not exposed to X-rays for a time period that is longer than a recommended time period (i.e. a predetermined time period) that may result in potentially unsafe exposure conditions for a patient. The backup method is activated to stop the generation of X-rays in the event that the primary method experiences a fault such that the generation of X-rays is not controlled and continues past the predetermined time period. In particular, the backup method is required to be able to terminate the X-rays if the X-ray exposure time period exceeds the predetermined time period by 10% (i.e. known as the 110% backup requirement).

A primary method of controlling X-rays is generally through a complex computational device or circuit such as a computer, microcomputer, FPGA, etc. The actual control is then performed by software/firmware. A disadvantage with this approach is that the software/firmware may have an error, flaw, failure or fault (i.e. a computer bug) or the computer can encounter some type of abnormal condition whereby it "hangs", "freezes", etc., thus allowing the generation of X-rays for longer than the predetermined time period and potentially resulting in unsafe conditions for a patient. Most systems also use programmable devices in the backup timer loop. Thus, the backup method is also prone to same disadvantages as the primary method. Further, it is relatively costly to demonstrate and/or prove to regulatory agencies that the backup method complies with government safety regulations. Further, compliance with safety regulations has to be demonstrated whenever a change is made to any program or computational device or circuit.

SUMMARY OF THE INVENTION

A timer circuit is disclosed for an X-ray imaging system having an X-ray generator used to generate images of a patient. The circuit includes a current sensor connected between a main power system and a circuit interrupter, wherein the circuit interrupter is also connected to the X-ray generator. The circuit also includes a timing device coupled between the current sensor and a control computer. The timing device is triggered when a current level detected by the current sensor exceeds an idle current level wherein X-rays are not generated by the X-ray generator. The timing device then measures a time period that the idle current level is exceeded. When the measured time period exceeds a predetermined time period by 10%, the circuit interrupter is activated to turn off current flow to the X-ray generator and stop X-ray generation.

Those skilled in the art may apply the respective features of the present invention jointly or severally in any combination or sub-combination.

BRIEF DESCRIPTION OF THE DRAWINGS

The exemplary embodiments of the invention are further described in the following detailed description in conjunction with the accompanying drawings, in which:

FIG. 1 depicts a backup safety timer circuit in accordance with an aspect of the invention.

To facilitate understanding, identical reference numerals have been used, where possible, to designate identical elements that are common to the figures. The figures are not drawn to scale.

DETAILED DESCRIPTION

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Regulatory agencies such as the FDA and IEC require primary and backup methods to stop the generation of, or terminate, X-rays so that a patient is not exposed to X-rays for a time period that is longer than a recommended time period (i.e. a predetermined time period). The backup method is activated to stop the generation of X-rays in the event that the primary method experiences a fault such that the generation of X-rays is not controlled and continues past the predetermined time period. In particular, the backup method is required to be able to terminate the X-rays if the X-ray exposure time period exceeds the predetermined time period by 10% (i.e. known as the 110% backup requirement).

Referring to FIG. 1, a backup safety timer circuit 10 in accordance with an aspect of the invention is shown. The timer circuit 10 serves as backup to the primary backup method described above and is activated in the event that the primary method experiences a fault such that the generation of X-rays is not controlled and continues past the predetermined time period. While the invention is directed to X-ray imaging systems, it is understood that the invention is also applicable to other radiation devices wherein it is desirable to limit a patient's exposure to radiation.

The timer circuit 10 is used in conjunction with a radiation device that generates radiation. In an embodiment, the radiation device may be an X-ray medical imaging system such as computed tomography (CT) system 12. The CT system 12 includes a CT gantry 14 having an X-ray generator 16, an X-ray detector assembly 18, a patient bore 20 for receiving a patient and various electronic hardware and software for generating CT scans. In accordance with an aspect of the invention, the timer circuit 10 includes a current sensor 22 connected between a main power system 24 and a circuit interrupter 26 connected to the X-ray generator 16. In an embodiment, the current sensor 22 includes a resistor 25 used for measuring current flow. When activated, the circuit interrupter 26 stops current flow to the X-ray generator 16. In an embodiment, the timer circuit 10 may be connected to a separate X-ray power line 28 used to supply power only to the X-ray generator 16 for the generation of X-rays. In particular, CT system 12 items such as cooling systems, anode spinning devices and others are not located on the power line 28. In an embodiment, the timer circuit 12 is located relatively close to input power. The timer circuit 10 also includes a timing device 30 that is coupled between the current sensor 22 and a control computer 32 that controls operation of the X-ray generator 16. The timing device 30 is activated or triggered when a predetermined current level is detected by the current sensor 22 as will be described.

When the CT system 12 is in an idle mode (i.e. when X-rays are not being generated by the X-ray generator 16), a relatively small current draw occurs on the power line 28 that forms an idle current level. A substantially higher current draw occurs on the power line 28 (i.e. an operational current level) when the X-ray generator 16 is activated to generate X-rays used for CT imaging, such as when the CT system 12 is set to its lowest exposure setting. In accordance with an aspect of the invention, the timing device 30 is triggered when the idle current level is exceeded, thus indicating that X-rays are being generated. The timing device 30 then measures the amount of time that the idle current level is exceeded, thus indicating a corresponding amount of time that the patient is exposed to X-rays. When the time period during which the idle current level is exceeded is greater than the predetermined time period, the circuit interrupter 26 is activated thus stopping current flow to the X-ray generator 16 and turning off the X-ray generator 16. In an embodiment, the circuit interrupter 26 is activated when the time period during which the patient is exposed to X-rays exceeds the predetermined time period by 10%. It is noted that 10% is an exemplary number. Embodiments of the invention may be triggered above or below the 10% trigger. For example, according to an embodiment of the invention, the circuit interrupter may be activated at 8% to allow a buffer against the maximum time period allowed for over radiation."

In addition, the timer circuit 10 of the invention may also be used to operate mandatory X-ray warning lights 34 of the CT system 12 when the predetermined time period is exceeded. Thus, aspects of the invention provide a backup safety timer circuit 10 that avoids the use of complex computational devices and associated software/firmware that may malfunction and provides a more reliable way to monitor whether X-rays are being generated and terminate X-ray exposure to the patient.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

We claim:

1. A timer circuit for a radiation device that generates radiation, comprising:
   a main power system;
   a circuit interrupter connected to the radiation device;
   a control computer;
   a current sensor connected between the main power system and the circuit interrupter, and
   a timing device coupled between the current sensor and the control computer, wherein the timing device is triggered when a current level detected by the current sensor exceeds a predetermined current level and, wherein the timing device measures a time period that the predetermined current level is exceeded, and wherein when the measured time period exceeds a predetermined time period, the circuit interrupter is configured to turn off current flow to the radiation device.

2. The timer circuit according to claim 1, wherein the radiation device is an X-ray imaging system having an X-ray generator and the predetermined current level is an idle current level when X-rays are not generated by the X-ray generator.

3. The timer circuit according to claim 1, wherein the circuit interrupter is activated when the measured time period exceeds the predetermined time period by 10%.

4. The timer circuit according to claim 1, wherein the current sensor includes a resistor.

5. The timer circuit according to claim 1, wherein the timing device triggers operation of warning lights when the predetermined time period is exceeded.

6. The timer circuit according to claim 1, wherein the timer circuit is a backup circuit that is activated when a primary method for detecting whether the predetermined time period is exceeded experiences a fault.

7. The timer circuit according to claim 1, wherein the current sensor is connected on a power line of the main power system that supplies power only to the radiation device.

8. A timer circuit for an X-ray imaging system having an X-ray generator used to generate images of a patient, comprising:
   a main power system;
   a circuit interrupter connected to the X-ray generator;
   a control computer;
   a current sensor connected between the main power system and the circuit interrupter, and
   a timing device coupled between the current sensor and the control computer, wherein the timing device is triggered when a current level detected by the current sensor exceeds an idle current level wherein X-rays are not generated by the X-ray generator, wherein the timing device measures a time period that the idle current level is exceeded, and wherein when the measured time period exceeds a predetermined time period by 10%, the circuit interrupter is configured to turn off current flow to the X-ray generator.

9. The timer circuit according to claim 8, wherein the current sensor includes a resistor.

10. The timer circuit according to claim 8, where the timing device triggers operation of X-ray warning lights when the predetermined time period is exceeded.

11. The timer circuit according to claim 8, wherein the timer circuit is a backup circuit that is activated when a primary method for detecting whether the predetermined time period is exceeded experiences a fault.

12. The timer circuit according to claim 8, wherein the current sensor is connected on a power line of the main power system that supplies power only to the X-ray generator.

13. A method of turning off an X-ray generator used to generate images of a patient, comprising:
providing a current sensor connected between a main power system and a circuit interrupter, wherein the circuit interrupter is connected to the X-ray generator;
triggering a timing device when a current level detected by the current sensor exceeds a predetermined current level;
measuring a time period that the predetermined current level is exceeded; and
activating the circuit interrupter to turn off current flow to the X-ray generator when the measured time period exceeds a predetermined time period.

14. The method according to claim 13, wherein the predetermined current level is an idle current level when X-rays are not generated by the X-ray generator.

15. The method according to claim 13, wherein the circuit interrupter is activated when the measured time period exceeds the predetermined time period by 10%.

16. The method according to claim 13, wherein the current sensor includes a resistor.

17. The method according to claim 13, where the timing device triggers operation of X-ray warning lights when the predetermined time period is exceeded.

18. The method according to claim 13, wherein a timer circuit includes the current sensor, the circuit interrupter, and the timing device, and wherein the timer circuit is backup circuit that is activated when a primary method for detecting whether the predetermined time period is exceeded experiences a fault.

19. The method according to claim 13, wherein the current sensor is connected on a power line of the main power system that supplies power only to the X-ray generator.

* * * * *